United States Patent
Reinauer et al.

(10) Patent No.: US 11,154,344 B2
(45) Date of Patent: Oct. 26, 2021

(54) CRANIAL BONE FASTENING DEVICE FOR FASTENING A CRANIAL BONE PORTION TO A POSITIONING DEVICE

(71) Applicant: Karl Leibinger Medizintechnik GmbH & Co. KG, Mühlheim (DE)

(72) Inventors: Frank Reinauer, Mühlheim (DE); Stefanie Grom, Mühlheim (DE); Anita Grigore, Mühlheim (DE); Veit Irion, Mühlheim (DE); Ernst-Johannes Haberl, Mühlheim (DE)

(73) Assignee: KARL LEIBINGER MEDIZINTECHNIK GMBH & CO. KG, Mühlheim (DE)

( * ) Notice: Subject to any disclaimer, the term of this patent is extended or adjusted under 35 U.S.C. 154(b) by 152 days.

(21) Appl. No.: 16/500,324

(22) PCT Filed: Apr. 4, 2018

(86) PCT No.: PCT/EP2018/058634
§ 371 (c)(1),
(2) Date: Oct. 2, 2019

(87) PCT Pub. No.: WO2018/185177
PCT Pub. Date: Oct. 11, 2018

(65) Prior Publication Data
US 2020/0107870 A1     Apr. 9, 2020

(30) Foreign Application Priority Data

Apr. 4, 2017   (DE) .................... 10 2017 107 261.6

(51) Int. Cl.
*A61B 17/88* (2006.01)
*A61B 17/68* (2006.01)
(Continued)

(52) U.S. Cl.
CPC .......... *A61B 17/8866* (2013.01); *A61B 17/60* (2013.01); *A61B 17/688* (2013.01); *A61B 17/8061* (2013.01); *A61B 90/14* (2016.02)

(58) Field of Classification Search
CPC ........................ A61B 17/8866; A61B 17/688
See application file for complete search history.

(56) References Cited

U.S. PATENT DOCUMENTS

| 276,135 | A | * | 4/1883 | Cooley | ................... F16B 33/02 411/366.1 |
| 5,423,858 | A | * | 6/1995 | Bolanos | ............. A61B 17/0057 24/297 |
| 6,379,363 | B1 | * | 4/2002 | Herrington | .......... A61B 17/688 606/104 |

(Continued)

FOREIGN PATENT DOCUMENTS

| DE | 19634696 | 4/1998 |
| DE | 201 01 793 | 5/2001 |

(Continued)

OTHER PUBLICATIONS

German Search Report dated Nov. 23, 2017 from German Application No. 10 2017 107 261.6.

(Continued)

*Primary Examiner* — Christian A Sevilla
(74) *Attorney, Agent, or Firm* — Beyer Law Group LLP

(57) ABSTRACT

A cranial bone fastening device for temporarily fastening multiple cranial bone portions to a main body of a positioning device in order to orient the cranial bone portions relative to one another, wherein a pin-like fixing element portion is provided, one side of which is designed to contact the multiple cranial bone portions in order to secure the cranial bone portions to the main body of the positioning device upon interaction with a counter portion on the other side of the cranial bone portions.

14 Claims, 2 Drawing Sheets

Figure 1:
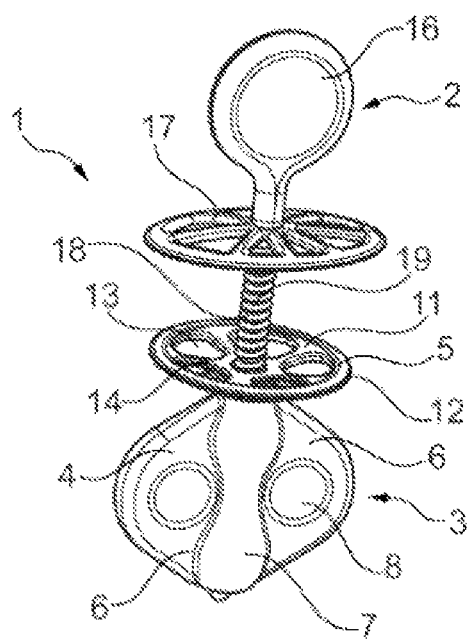

(51) Int. Cl.
*A61B 17/80* (2006.01)
*A61B 17/16* (2006.01)
*A61B 17/60* (2006.01)
*A61B 90/14* (2016.01)

(56) References Cited

U.S. PATENT DOCUMENTS

| | | | | |
|---|---|---|---|---|
| 6,685,707 | B2* | 2/2004 | Roman | A61B 17/688 606/213 |
| 2002/0169455 | A1* | 11/2002 | Bannerman | A61B 17/8869 606/99 |
| 2003/0229349 | A1 | 12/2003 | Wellisz et al. | |
| 2004/0210224 | A1* | 10/2004 | Ahmad | A61B 17/688 606/916 |
| 2008/0039837 | A1 | 2/2008 | Gambale | |
| 2014/0135852 | A1 | 5/2014 | Memmolo et al. | |

FOREIGN PATENT DOCUMENTS

| | | |
|---|---|---|
| DE | 297 24 708 | 2/2003 |
| FR | 2 928 824 | 3/2008 |
| RU | 2410056 | 1/2011 |
| RU | 2410057 | 1/2011 |
| RU | 2668199 | 9/2018 |
| WO | WO 2014/072082 | 5/2014 |
| WO | WO 2014/174538 | 10/2014 |

OTHER PUBLICATIONS

International Search Report dated Jul. 13, 2018 from International Application No. PCT/EP2018/058634.
Russian Examination and Search Report dated Jul. 12, 2021 from Russian Application No. 2019133589/14 (066289).

* cited by examiner

CRANIAL BONE FASTENING DEVICE FOR FASTENING A CRANIAL BONE PORTION TO A POSITIONING DEVICE

The invention relates to a cranial bone fastening device/fastening device for temporary fastening of a cranial bone portion or several cranial bone portions to a primary body of a positioning device, wherein the positioning device is designed to orientate the cranial bone portions relative to each other and to adapt them to the shape of the positioning device.

The prior art already shows fastening devices, which act in a fixing manner when arranging the cranial bone portions. Inter alia, WO 2014 072 082 A1 discloses a system for fastening, intended to aid in the surgical correction of malformed regions of the skull, wherein the system is arranged around a skull template corresponding to the size and desired head form of a patient, the system comprising a supporting stand for fixing a holding frame at its lateral ends in such a manner that the holding frame is freely rotatable and fixable in any angle, wherein the skull template is firmly connected to the holding frame; said holding frame providing means for fixation of at least one bowed clamp-frame, wherein at least one clamp-holder for taking up a clamp-plunger and at least one fixation pin for fixation of bone pieces can be fixed to the at least one bowed clamp-frame.

However, the state of the art always has the disadvantage that the conventional fastening devices are designed in such a way that it takes a very long time to fasten the fastening devices to a cranial bone portion or a positioning device. Another problem is that the cranial bone portions often cannot be securely fixed and therefore require the time-consuming use of many fastening devices in the form of a clamping pin or the like, since the fastening mechanism of the fastening devices does not grip securely, in particular in the case of small-caliber/weak bones. Using many fastening devices that respectively perforate the bone and thus leave a perforation in the bone restricts the selection of the later final fixation points by means of resorbable plate material, since no secure hold of the plate fixation elements is guaranteed in the perforation left behind.

It is therefore the object of the invention to avoid or at least mitigate the disadvantages of the prior art. In particular, a cranial bone fastening device is to be developed that can be attached quickly and easily. The total duration of the surgery can thus be reduced.

The object of the invention is solved in accordance with the invention by a pin-like fixing element portion provided in the cranial bone fastening device, which is designed for one-sided, direct contacting of the cranial bone portion or of several cranial bone portions on one side, in order to fix it or them to the primary body of the positioning device when form-fittingly and/or force-fittingly interacting with a counter portion on the other side of the cranial bone portion or of the cranial bone portions.

This has the advantage that the cranial bone portion or the cranial bone portions can be securely fixed to the primary body of the positioning device, in particular without damaging the cranial bone portion by perforation.

Advantageous embodiments are claimed in the dependent claims and are explained in more detail below.

In addition, it is practical if the fixing element portion and the counter portion are configured in such a way that they engage in each other in the fastening state. This effectively prevents the connection between the fixing element portion and the counter portion from unintentionally loosening, so that the cranial bone portion can no longer be held sufficiently in its position.

It is furthermore advantageous if the cranial bone fastening device is constructed in at least two parts, and one part of the cranial bone fastening device forms the fixing element portion and another part of the cranial bone fastening device forms the counter portion. Thus one part, i.e. the fixing element portion, can be pressed from one side against the cranial bone portions and the other part, i.e. the counter portion, can be arranged on the other side of the cranial bone portions, i.e. pressed against the primary body. Since the primary body of the positioning device has recesses, part of the fixing element portion can reach through the positioning device and engage the counter portion, so that the cranial bone portion is clamped/fixed to the primary body of the positioning device.

In addition, it is advantageous if the fixing element portion has a pin designed to extend from one side of the cranial bone portion to the other side of the cranial bone portion in the fixed state and to engage in the counter portion there. Thus, the fixing element portion can be placed on the positioning device from one side and the counter portion can be placed on it from the other side, and at the same time interlocking via the pin of the fixing element portion can be ensured by the positioning device. The pin can reach through the gap between the cranial bone portions. In an alternative form of application, however, it is also possible to guide the pin directly through a cranial bone portion, which would, however, lead to a perforation of the cranial bone.

It is furthermore advantageous if the fixing element portion and the counter portion are materially separated from each other. This allows the two portions to be arranged freely from each other at first and then fixed to each other using the pin. This allows the fastening device to be used flexibly.

A favorable exemplary embodiment is also distinguished by the fact that the counter portion is designed to receive the fixing element portion in such a way that the cranial bone portion is fastened to the positioning device.

It is also practical if the counter portion has both a handle region for being grasped by a plurality of fingers of a surgeon or a tool as well as a bracing region for contacting the positioning device or the cranial bone portion. Thus, it is exactly separated at which part of the counter portion the counter portion is gripped and at which part of the counter portion the counter portion is placed on the cranial bone portion or the positioning device.

It is furthermore advantageous if the bracing region of the counter portion is geometrically matched to the positioning device or the cranial bone portion for flat or 3-point contact on a surface adjacent to the positioning device or the cranial bone portion. This prevents the counter portion from slipping relative to the cranial bone portion or the positioning device in the fastening state.

It is also advantageous if the bracing region of the counter portion is plate-shaped, since it can thus fit particularly well to the outer shape of the positioning device or the cranial bone portion or lie against it.

It is also practical if the bracing region of the counter portion is formed as a concave shell/concave wreath/with a concave surface facing the cranial bone portion. In particular, the bracing region can thus advantageously lie flat against the cranial bone portion or the positioning device.

Moreover, it is particularly advantageous if the bracing region is oval, ellipsoidal, egg-shaped, round, circular or star-shaped. This means that even several cranial bone fastening devices can be arranged on the cranial bone portion or the positioning device without considerably restricting the freedom of arrangement of the several cranial bone fastening devices. Rather, it allows the cranial bone portions to be securely held and, at the same time, that an area as small as possible is blocked.

The bracing region can also be star-shaped with five tips, which are preferably rounded, since the bracing region thus has an optimized ratio between force distribution and support surface.

It is furthermore practical if the bracing region of the counter portion is designed in such a way that it lies with the concave surface on the positioning device or the cranial bone portion. In this way, the cranial bone fastening device adapts particularly well to the shape of the surface of the cranial bone portion or the positioning device.

It is furthermore advantageous if the bracing region of the counter portion has one or more recesses, since it thus has a reduced weight and increased transparency and thus significantly improves handling and optical control.

In particular, the recesses in the bracing region may be separated from each other by struts, since this still ensures sufficiently high stability and strength for the counter portion, even with a reduced contact area of the bracing region.

Another advantage is when the counter portion has a thread, in particular an inside thread, which is designed to accommodate a part of the fixing element portion. Threads are particularly easy to produce and provide a secure receptacle for an appropriately designed counter element so that the counter element cannot accidentally come loose from the thread. At the same time, fastening in a thread is particularly simple and can also be done with one hand. It is particularly advantageous if the thread is arranged perpendicular to the bracing region.

A favorable exemplary embodiment is also distinguished by the fact that the counter portion is produced in a generative manufacturing method. In this way, the shape of the counter portion can be individually adapted and can be produced cost-effectively and within a short time.

It is also possible that the counter portion is produced by injection molding, in particular from plastic, such as thermoplastics, e.g. a polyamide. Injection molding allows the counter portion to be produced even more cost-effectively than in a generative manufacturing method and in larger quantities. In addition, it is possible for a material to have optimal properties, e.g. with regard to sterilizability.

It is also advantageous if the handle region of the counter portion is plate-like, since the handle region can be grasped more easily by fingers or a tool.

In particular, it is also advantageous if the handle region of the counter portion has two wings, since two fingers can be placed on the handle region particularly well. In a preferred exemplary embodiment, the two wings project on both sides approximately at the height of the thread in a plane.

In addition, the handle region of the counter portion may have one or more indentations. The indentations are in particular round and dimensioned to fit fingers or fingertips. This provides an even better hold when gripping the counter portion.

Moreover, it is practical if the handle region of the counter portion has a thickening, in particular at a distal end. It is particularly preferred if the indentations are arranged adjacent to the thickening.

The thickening can in particular extend in the longitudinal direction. It is also advantageous if the thread is arranged inside the thickening.

It is also advantageous if the thickening is thinner in a central area in the longitudinal direction than in an edge area arranged in the longitudinal direction. The longitudinal direction is the direction extending from the bracing region to the handle region, i.e. the direction in which the thread extends.

Moreover, it is advantageous if there is a recess in the counter portion in the form of a through bore that extends longitudinally through the middle of the bracing region and the handle region, in particular within the thickening. Preferably, the thread/inside thread is formed in this through bore.

A further favorable exemplary embodiment is distinguished by the fact that the fixing element portion comprises a handle region for being gripped by fingers of a surgeon or by a tool, a support region for being supported on a cranial bone portion or on the positioning device, and a coupling region for being received by the counter portion, in particular by the thread and the through bore of the counter portion.

The coupling region can also be designed to be received by the counter portion. In this way, the cranial bone portion can be fixed to the positioning device between the counter portion and the fixing element portion via the coupling region.

In particular, the coupling region can penetrate recesses on the positioning device and can additionally penetrate between a gap of two cranial bone portions or through a cranial bone portion.

It is also advantageous if the coupling region is designed in the manner of a pin, since in this way it can easily reach the other side of the cranial bone portion and the positioning device. In addition, the coupling region can also reach through smaller recesses and/or cause only a small hole in the cranial bone portion.

Furthermore, it is advantageous if the coupling region has a thread region with a thread, in particular an outside thread. This allows the coupling region to engage in particular with an inside thread of the counter portion.

It is particularly advantageous if the outside thread is designed to be screwed into the inside thread of the counter portion. This allows a force-fit connection to be established between the counter portion and the fixing element portion of the cranial bone fastening device.

Furthermore, it is preferred if a thickening is provided at a distal end of the coupling region. It is particularly advantageous if the thickening is geometrically matched to the recess in the way of the through bore of the counter portion.

The thickening is advantageously larger than the diameter at a tapered site/tapering of the recess, since the thickening can thus serve as loss protection. During application, the coupling region is pushed through the recess in the counter element.

It is moreover advantageous if the thickening is elastically deformable so that the coupling region can be passed through the tapering within the recess. The thickening is therefore preferably designed in such a way that its thickness allows it to pass through the recess when it is elastically deformed, but that it does not fit through the recess in its undeformed shape without exerting force.

It is moreover advantageous if the coupling region has the proximal thread region and the adjacent, threadless end pin, which has the thickening at the distal end.

Furthermore, it is advantageous if the length of the threadless end pin is greater than the length of the through bore of the counter portion, so that the end pin can be pushed through the through bore before the thread of the coupling region engages the thread of the through bore.

It is also advantageous if there is a predetermined breaking point at the coupling region, in particular at the point where the coupling region transitions into the support region, which is designed to break off at a predetermined force. In particular, the coupling region breaks off from the support region if the fixing element portion is screwed too far into the counter portion, so that the support region is pressed against the bracing region or the cranial bone portion and the two portions counteract each other.

It is also advantageous if the handle region of the fixing element portion has an indentation so that the handle region can be grasped more easily and slippage of the fixing element portion is prevented.

It is also advantageous if the handle region of the fixing element portion has an anti-slip surface so that the adhesion between a tool or a gripping finger is increased and slippage is prevented.

Moreover, it is practical if the support region of the fixing element portion is geometrically matched to the cranial bone portion or the positioning device on its surface adjacent to the cranial bone portion or the positioning device.

In particular, the support region of the fixing element portion can be designed as a concave shell/with a concave surface or curved, in particular on the surface facing away from the coupling region, since in this way it fits particularly well to the surface of the cranial bone portion or the positioning device.

It is also advantageous if the support region of the fixing element portion is plate shaped. In this way, the pressure is advantageously distributed over a larger area of the cranial bone portion or the positioning device and thus offers greater stability during fixation.

It is moreover advantageous if the support region of the fixing element portion is oval, ellipsoidal, egg-shaped, round, circular, or star-shaped. This makes it possible that several fastening devices can be arranged even on a small surface.

A favorable exemplary embodiment is distinguished by the fact that the support region of the fixing element portion has one or more recesses, since it thus has a reduced weight and advantageously improves handling. Moreover, the material costs and above all the manufacturing time are thus considerably reduced.

The cranial bone fastening device is also preferably designed in such a way that the coupling region adjoins the surface of the fixing element portion which is in contact with the cranial bone portion or the positioning device. The coupling region therefore transitions into the support region and then into the coupling region with a thread region and a threadless support region and finally into the thickening.

Preferably, the fixing element portion is produced by a generative method. The fixing element portion can also be produced by injection molding, since this considerably reduces costs and time required to produce a fixing element portion.

It is furthermore advantageous if the fixing element portion consists of or includes polyamide or another plastic, since these have particularly good properties in terms of weight, costs and medical applicability.

In addition, it is practical if the cranial bone fastening device is used in a procedure for the surgical correction of deformed cranial bones. In one surgery step the deformed cranial bone portions are removed, in a second surgery step the removed cranial bone portions are arranged on an inner surface of a positioning device corresponding to the individual, desired shape of the skull and orientated towards each other so that they form an approximately closed surface corresponding to the desired shape of the skull. The orientated cranial bone portions are attached to the positioning device with one or more cranial bone fastening devices/fastening devices according to the invention.

Afterwards, the cranial bone portions brought into the adapted shape can be fixed to each other via approximately strip-shaped implants of different length and width, so that they maintain their position in relation to each other permanently. The cranial bone fastening devices can then be detached from the positioning device and the cranial bone portions. Subsequently, the cranial bone portions firmly fastened to each other can be removed from the positioning device and can be implanted back into the skull.

Figure 2:
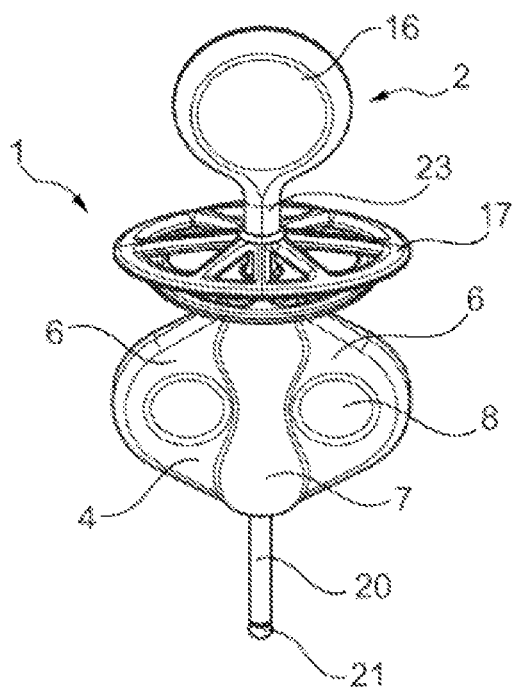
Figure 3:
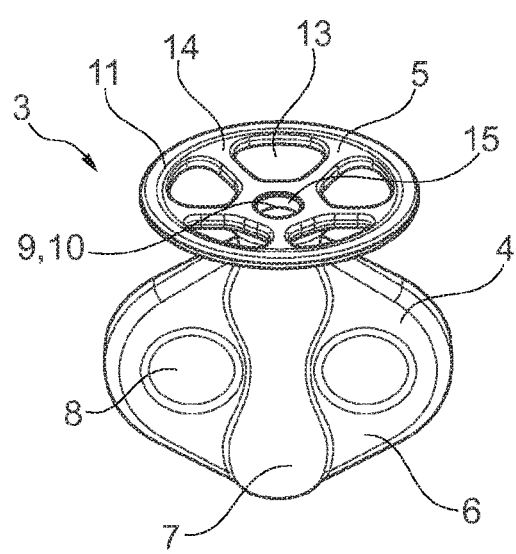
Figure 4:
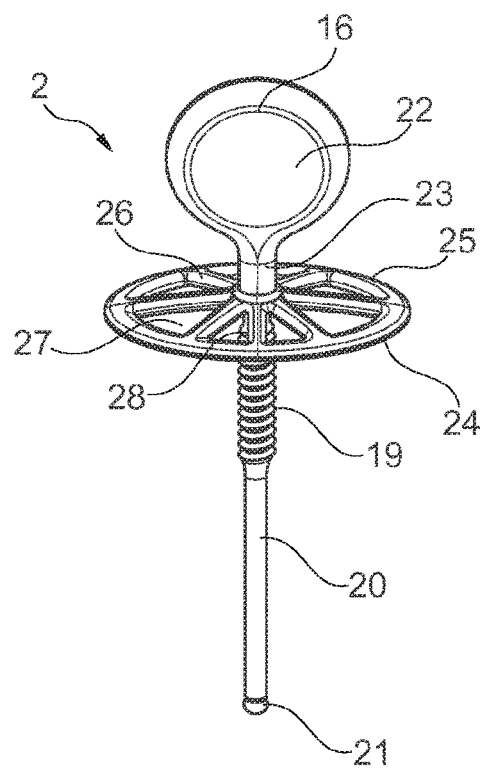
Figure 5:
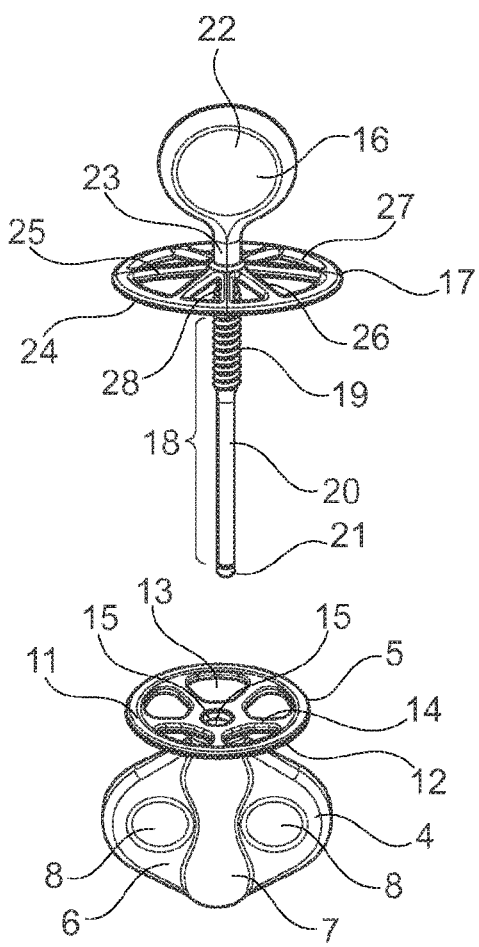

The invention is explained in the following with the help of the drawings. These show:

FIG. 1 shows a perspective view of a cranial fastening device according to the invention with a counter portion and a fixing element portion, FIG. 2 shows a perspective view of the cranial bone fastening device with the fixing element portion screwed into the counter portion, FIG. 3 shows a perspective view of the counter portion with a handle region and a bracing region, FIG. 4 shows a perspective view of the fixing element portion with a handle region, a support region and a coupling region, and FIG. 5 shows the cranial fastening device in a perspective view.

The figures are merely schematic in nature and serve exclusively to understand the invention. The same elements are provided with the same reference signs.

FIG. 1 shows a cranial bone fastening device 1 which is designed for temporarily fastening a cranial bone portion to a primary body of a positioning device. The cranial bone fastening device 1 has a fixing element portion 2 and a counter portion 3. The fixing element portion 2 is pin-shaped and designed to contact the cranial bone portion or several cranial bone portions on one side while interacting with the counter portion 3 arranged on the other side of the cranial bone portion or portions.

The counter portion 3 has a handle region 4 and a bracing region 5. The handle region 4 is plate-like and two wings 6 which protrude from both sides of a thickening 7 in the same plane. A round, circular indentation 8 is formed on each wing 6. The two indentations 8 are arranged on both sides of the thickening 7 at the same distance. The thickening 7 is arranged in a longitudinal direction of the handle region 4. Inside the thickening 7, a recess 9 is arranged longitudinally in the manner of a through bore 10.

The thickening 8 is of non-constant thickness so that it has a larger diameter in the two edge regions arranged in the longitudinal direction than in the middle region arranged in the longitudinal direction. The handle region 4 of the counter portion 3 has a coating that acts in a particularly anti-slip, i.e. slip-resistant, manner. The handle region 4 of counter portion 3 transitions into the bracing region 5 of counter portion 3.

The bracing region 5 extends approximately plate-like into a plane which is orthogonal to the longitudinal direction of the counter portion 3. The bracing region 5 having a round or alternatively oval outer contour is thus formed in such a way that it has a concave surface 11 and a convex surface 12, which together form a convex shell of the bracing region 5. The convex surface 12 of the bracing region 5 is the side facing the handle region 4. The concave surface 11, on the other hand, is the surface of the bracing region 5 which is facing away from the handle region 4, i.e. facing the fixing element portion 2 and in the mounted state the cranial bone portion or the positioning device.

The bracing region 5 is formed to be round and has recesses 13, which are separated from each other by webs 14. An inside thread 15 is integrated in the through bore 10 within the thickening 7 of the handle region 4 and the bracing region 5. The inside thread 15 can extend over the entire length of the through bore 10 or only over a section of the through bore 10.

The counter portion 3 of the cranial bone fastening device 1 is engaged by the fixing element portion 2 in the mounted state. The fixing element portion 2 consists of a handle region 16, which transitions via a web 23 into a support region 17, wherein the support region 17 is followed by a coupling region 18. The coupling region 18 consists of a thread region 19 and a threadless end pin 20, which ends with a thickening 21. The thread region 19 has an outside thread, which is adjusted to the counter portion 3 in such a way that the outside thread of the thread region 19 can engage with the inside thread 15 in the through bore 10.

FIG. 2 shows the cranial bone fastening device 1 in a state in which the fixing element portion 2 with its thread region 19 is screwed into the inside thread 15 of the counter portion 3. The cranial bone portion is fixed to the positioning device between the bracing region 5 of the counter portion 3 and the support region 17 of the fixing element portion 2 during use.

FIG. 3 shows an enlarged view of the counter portion 3. Here, it is particularly easy to see that the inside thread 15 is formed in the through bore 10. The counter portion 3 is arranged either on the inside of the positioning device or on the outside of the positioning device. Since the cranial bone portions are arranged on the inside of the positioning device, the counter portion 3 contacts either the cranial bone portions on the inside, in particular with its bracing region 5, or the lattice structure of the positioning device on the outside.

FIG. 4 shows an enlarged view of the fixing element portion 2. The handle region 16, which has a central indentation 22, transitions into the support region 17 via the small web 23. The support region 17 is formed like an oval plate. Equivalent to the bracing region 5, the support region 17 has a concave surface 24 which is arranged on the side facing the coupling region 18 and which is configured to contact the cranial bone portion or the positioning device, and has a convex surface 25 which is arranged on the side facing the handle region 16. The support region 17 is formed by webs 26, which separate several approximately triangular recesses 27 from each other.

The coupling region 18 is connected centrally to the support region 17. Between the support region 17 and the thread region 19, there is a thinned section of the coupling region 18, which serves as a predetermined breaking point 28 for protection against incorrect use. The predetermined breaking point 28 ensures that the coupling region 18 breaks off from the support region 17 when an excessive force is applied in the axial direction or in a direction orthogonal or inclined to the axial direction. The predetermined breaking point 28 is adjoined by the thread region 19, which is matched to the inside thread 15 of counter portion 3.

The thread region 19 transitions into a threadless end pin 20. The end pin 20 is matched to the counter portion 3 in such a way that the length of the end pin 20 is at least as large as the length of the entire counter portion 3 in the longitudinal direction. This has the purpose that the end pin 20 can be passed through the through bore 10 of the counter portion 3 without the inside thread 15 and the thread region 19 interlocking. The thickening 21 is arranged at a distal end of the end pin 20. It has a diameter that is smaller than the diameter of the through bore 10, but larger than a tapered site/tapering in the through bore 10. The thickening 21 thus serves as a loss protection. When inserting the fixing element portion 2, the thickening 21 is elastically deformed so that it can be passed through the tapered site in the through bore 10. The thickening 21 thus prevents the fixing element portion 2 from slipping back through the through bore 10 of the counter portion 3 without any application of force.

FIG. 5 shows the two portions 2, 3 of the cranial-bone fastening device 1 in a state in which they do not interact. For fastening the fixing element portion 2, it is pushed through the through bore 10 of the counter portion 3 with its coupling region 18. The cranial bone portions to be fastened are clamped together with the positioning device between the support region 17 and the bracing region 5. The coupling region 18 can either be passed through the cranial bone portions or it can be arranged between several cranial bone portions. The coupling region thus engages the counter portion 3 in such a way that the cranial bone portions are attached via the bracing region 5 and the support region 17, since they are held between the bracing region 5 and the support region 17 at the positioning device.

LIST OF REFERENCE SIGNS 1 cranial bone fastening device
2 fixing element portion
3 counter portion
4 handle region
5 bracing region
6 wing
7 thickening
8 indentation
9 recess
10 through bore
11 concave surface
12 convex surface
13 recess
14 web
15 inside thread
16 handle region
17 support region
18 coupling region
19 thread region
20 end pin
21 thickening
22 indentation
23 web
24 concave surface
25 convex surface
26 web
27 recess
28 predetermined breaking point

The invention claimed is:

1. A cranial bone fastening device for temporary fastening of several cranial bone portions to a positioning device in order to orientate the cranial bone portions relative to each other, the cranial bone fastening device comprising a pin-shaped fixing element portion and a counter portion, the fixing element portion having a support surface shaped to contact the several cranial bone portions on one side of the cranial bone portions while interacting with the counter portion, the counter portion having a bracing surface arranged to contact the other side of the cranial bone portions to fasten them on the positioning device, wherein the fixing element portion and the counter portion are separable so as not to be connected during mounting and detaching, wherein the fixing element portion has a pin dimensioned to extend along a pin axis from one side of the cranial bone portions to the other side of the cranial bone portions and engage the counter portion while the cranial bone fastening device is in a fixed state, the fixing element portion comprising a handle portion extending radially outward from the pin axis while projecting outwardly in a direction away from and opposite the support surface from the pin, the counter portion having a handle portion extending radially outward from the pin axis when in the fixed state while projecting outwardly in a direction away from the bracing surface.

2. The cranial bone fastening device according to claim 1, wherein the fixing element portion and the counter portion are designed to engage with each other in the fixed state.

3. The cranial bone fastening device according to claim 1, wherein the cranial bone fastening device is constructed at least in two parts and one part of the cranial bone fastening device forms the fixing element portion and another part of the cranial bone fastening device forms the counter portion.

4. The cranial bone fastening device according to claim 1, wherein the fixing element portion and the counter portion are materially separated from each other.

5. The cranial bone fastening device according to claim 1, wherein the fixing element portion is configured to be guided from one side against the cranial bone portions when being mounted, and the counter portion is configured to be guided from the other side of the cranial bone portions against the positioning device when being mounted.

6. The cranial bone fastening device according to claim 1, wherein the handle portion of the counter portion is shaped for being grasped by a plurality of fingers of a surgeon or a tool, and the bracing surface is disposed on a bracing region for contacting the positioning device or the cranial bone portion.

7. The cranial bone fastening device according to claim 6, wherein the bracing surface of the counter portion is geometrically matched to the positioning device or the cranial bone portions at a surface adjacent to the positioning device or the cranial bone portion.

8. The cranial bone fastening device according to claim 6, wherein the bracing region of the counter portion has a plate-like shape.

9. The cranial bone fastening device according to claim 6, wherein the bracing region of the counter portion is formed as a concave shell, the bracing surface comprising a concave surface configured to face the cranial bone portions when the cranial bone fastening device is in the fixed state.

10. The cranial bone fastening device according to claim 1, wherein one or more of the handle portion of the fixing element portion and the handle portion of the counter portion have a plate-like configuration.

11. The cranial bone fastening device according to claim 1, wherein one or more of the handle portion of the fixing element portion and the handle portion of the counter portion have a recess serving as a grasping recess.

12. The cranial bone fastening device according to claim 1, wherein one or more of the handle portion of the fixing element portion and the handle portion of the counter portion have an anti-slip coating.

13. The cranial bone fastening device according to claim 1:
wherein the counter portion comprises a through bore for receiving the pin of the fixing element portion along the pin axis; and
wherein the handle portion of the counter portion has a thickening at least partially encircling the through bore, the handle portion of the fixing element portion comprising two opposing grip wings arranged on opposite sides of the thickening.

14. The cranial bone fastening device according to claim 13, wherein the thickening has a variable thickness in a longitudinal direction along the through bore of the handle portion.

* * * * *